(12) United States Patent
Shibata et al.

(10) Patent No.: US 11,284,865 B2
(45) Date of Patent: Mar. 29, 2022

(54) ULTRASONIC DIAGNOSTIC APPARATUS AND METHOD FOR CONTROLLING PULSE REPETITION FREQUENCY

(71) Applicant: CANON MEDICAL SYSTEMS CORPORATION, Otawara (JP)

(72) Inventors: Chihiro Shibata, Nasushiobara (JP); Akihiro Kakee, Nasushiobara (JP); Kuramitsu Nishihara, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 286 days.

(21) Appl. No.: 16/214,612

(22) Filed: Dec. 10, 2018

(65) Prior Publication Data

US 2019/0175147 A1 Jun. 13, 2019

(30) Foreign Application Priority Data

Dec. 12, 2017 (JP) .............................. JP2017-237952
Dec. 4, 2018 (JP) .............................. JP2018-227400

(51) Int. Cl.
*A61B 8/08* (2006.01)
*A61B 8/15* (2006.01)
*G06T 7/11* (2017.01)
*A61B 8/00* (2006.01)
*G06T 7/12* (2017.01)
*G01S 7/52* (2006.01)

(52) U.S. Cl.
CPC .............. *A61B 8/5207* (2013.01); *A61B 8/15* (2013.01); *A61B 8/466* (2013.01); *A61B 8/483* (2013.01); *A61B 8/488* (2013.01); *A61B 8/54* (2013.01); *G01S 7/52017* (2013.01); *G06T 7/11* (2017.01); *G06T 7/12* (2017.01); *G06T 2207/10132* (2013.01); *G06T 2207/20021* (2013.01)

(58) Field of Classification Search
CPC .......... A61B 8/15; A61B 8/466; A61B 8/483; A61B 8/488; A61B 8/5207; A61B 8/54; G01S 15/8915; G01S 7/52017; G01S 7/5202; G01S 7/52063; G01S 7/52085; G06T 2207/10132; G06T 2207/20021; G06T 7/11; G06T 7/12
See application file for complete search history.

(56) References Cited

U.S. PATENT DOCUMENTS

2011/0245677 A1* 10/2011 Sato .................... G01S 7/52079
600/447
2012/0328156 A1* 12/2012 Nakano ................... G06T 7/181
382/103

(Continued)

FOREIGN PATENT DOCUMENTS

JP 2016-190032 11/2016

*Primary Examiner* — Pascal M Bui Pho
*Assistant Examiner* — Alexei Bykhovski
(74) *Attorney, Agent, or Firm* — Oblon, McClelland, Maier & Neustadt, L.L.P.

(57) ABSTRACT

The ultrasonic diagnostic apparatus according to the present embodiment includes processing circuitry. The processing circuitry is configured to determine a scan region of an ultrasonic wave according to a scan target. The processing circuitry is configured to set a pulse repetition frequency for each raster of rasters so as to correspond to the scan region. The processing circuitry is configured to control a scan performance according to the pulse repetition frequency.

14 Claims, 10 Drawing Sheets

(56) References Cited

U.S. PATENT DOCUMENTS

2013/0281855 A1\* 10/2013 Baba .................... A61B 8/5207
  600/441
2016/0287214 A1   10/2016 Ralovich et al.
2017/0224309 A1\*  8/2017 Imamura ................ A61B 8/488

\* cited by examiner

| | DIVISION NUMBER (u) | BLOCK | SEQUENCE OF ULTRASONIC TRANSMITTING AND RECEIVING |
|---|---|---|---|
| SEQUENCE 1 | 0 | – | RASTER L1, L2, L3, L4, ⋯, L12 |
| SEQUENCE 2 | 2 | FIRST BLOCK : RASTER L1-L6 SECOND BLOCK : RASTER L7-L12 | RASTER L1, L7, L2, L8, ⋯, L12 |
| SEQUENCE 3 | 4 | FIRST BLOCK : RASTER L1-L3 SECOND BLOCK : RASTER L4-L6 THIRD BLOCK : RASTER L7-L9 FOURTH BLOCK : RASTER L10-L12 | RASTER L1, L4, L7, L10, L2, L5, ⋯, L12 |

FIG. 10B

ULTRASONIC DIAGNOSTIC APPARATUS AND METHOD FOR CONTROLLING PULSE REPETITION FREQUENCY

CROSS-REFERENCE TO RELATED APPLICATION

This application is based upon and claims the benefit of priority from Japanese Patent Application No. 2017-237952, filed on Dec. 12, 2017, and Japanese Patent Application No. 2018-227400, filed on Dec. 4, 2018, the entire contents of each of which are incorporated herein by reference.

FIELD

An embodiment as an aspect of the present invention relates to an ultrasonic diagnostic apparatus and a method for controlling a pulse repetition frequency.

BACKGROUND

In the medical field, an ultrasonic diagnostic apparatus is used for imaging the inside of a subject using ultrasonic waves generated by multiple transducers (piezoelectric transducers) of an ultrasonic probe. The ultrasonic diagnostic apparatus causes the ultrasonic probe, which is connected to the ultrasonic diagnostic apparatus, to transmit ultrasonic waves into the subject, generates an echo signal based on a reflected wave, and obtains a desired ultrasonic image by image processing.

In the conventional ultrasonic diagnostic apparatus, a B mode image which is the ultrasonic image processed in the B mode based on the echo signal is used in order to grasp the structure of an organ or the like. The B mode image is a so-called black and white image, and is an image expressing a difference in structure depending on a difference in luminance value. In the B mode image, since the reflection state of the ultrasonic waves is different depending on the difference in the tissue, it is possible to clearly express the boundary or the like with respect to the portions having different tissue properties largely.

Since the pulse repetition frequency (PRF) determined by the scan region used in the ultrasonic diagnostic apparatus and the depth of the scan region is predetermined before the scan. The PRF cannot be changed each time it is scanned, and the PRF cannot be changed each time it is scanned according to the change of the scan target due to individual differences. Therefore, when forcibly trying to change the PRF, a region having a depth necessary for diagnosis may be excluded from the scan region, or a region with a depth unnecessary for diagnosis may be included in the scan region.

BRIEF DESCRIPTION OF THE DRAWINGS

Each of FIGS. 4A to 4C is a diagram for explaining a method for setting a second PRF according to the scan target in the ultrasonic diagnostic apparatus according to the present embodiment.

Each of FIGS. 5A to 5C is a diagram for explaining a method for setting a second PRF in the ultrasonic diagnostic apparatus according to the present embodiment when the scan target is the heart.

Each of FIGS. 6A to 6C is a diagram for explaining a method for setting a second PRF in the ultrasonic diagnostic apparatus according to the present embodiment when the scan target is the abdomen.

Each of FIGS. 7A and 7B is a diagram for explaining a method for setting a second PRF in the ultrasonic diagnostic apparatus according to the present embodiment when the scan target is the abdomen.

Each of FIGS. 8A to 8C is a diagram for explaining a method for setting a second PRF in the ultrasonic diagnostic apparatus according to the present embodiment when the scan target is a fetus.

Each of FIGS. 10A and 10B is a diagram showing a sequence of ultrasonic transmission and reception performed in rasters in the second scan region, in the ultrasonic diagnostic apparatus according to the present embodiment.

DETAILED DESCRIPTION

An ultrasonic diagnostic apparatus and a method for controlling a pulse repetition frequency according to a present embodiment will be described with reference to the accompanying drawings.

The ultrasonic diagnostic apparatus according to the present embodiment includes processing circuitry. The processing circuitry is configured to determine a scan region of an ultrasonic wave according to a scan target. The processing circuitry is configured to set a pulse repetition frequency for each raster of rasters so as to correspond to the scan region. The processing circuitry is configured to control a scan performance according to the pulse repetition frequency.

1. Ultrasonic Diagnostic Apparatus According to Present Embodiment

Figure 1:
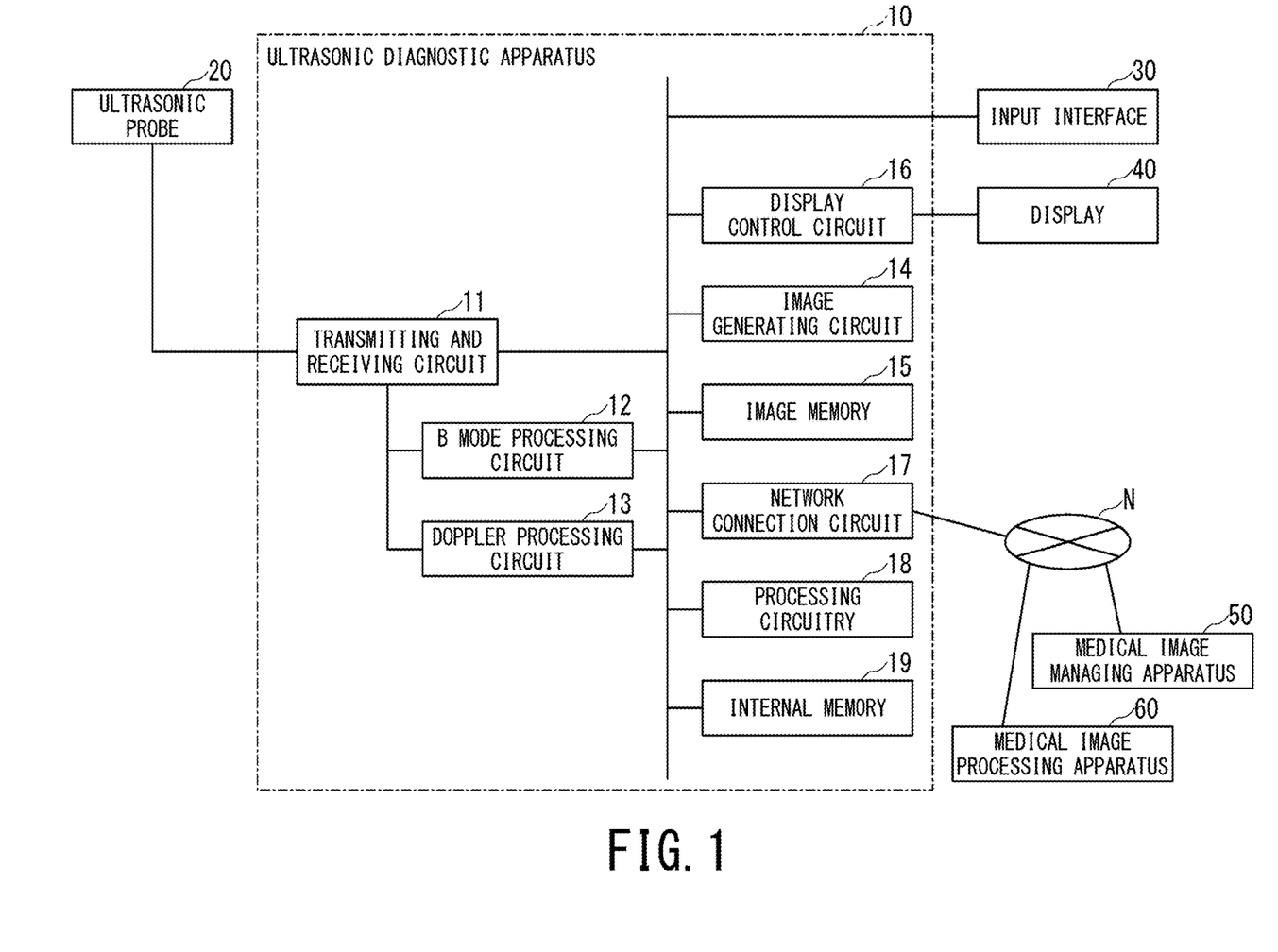
FIG. 1 is a schematic diagram showing a configuration of an ultrasonic diagnostic apparatus according to a present embodiment.

FIG. 1 is a schematic diagram showing a configuration of an ultrasonic diagnostic apparatus according to a present embodiment.

FIG. 1 shows an ultrasonic diagnostic apparatus 10 according to a present embodiment. FIG. 1 shows an ultrasonic probe 20, an input unit (for example, an input interface) 30, and a display unit (for example, a display) 40. It should be noted that a device in which at least one of the ultrasonic probe 20, the input interface 30, and the display 40 is added to the ultrasonic diagnostic apparatus 10 may be referred to as an ultrasonic diagnostic apparatus in some cases. In the following description, a case where all of the ultrasonic probe 20, the input interface 30, and the display 40 are provided outside the ultrasonic diagnostic apparatus 10 will be described.

The ultrasonic diagnostic apparatus 10 includes a transmitting and receiving unit (for example, a transmitting and receiving circuit) 11, a B mode processor (for example, a B mode processing circuit) 12, a Doppler processor (for example, a Doppler processing circuit) 13, an image generator (for example, an image generating circuit) 14, an image storage (for example, an image memory) 15, a display controller (for example, a display control circuit) 16, a network connector (for example, a network connection circuit) 17, a processor (for example, processing circuitry) 18, and a storage (for example, an internal memory) 19. The circuits 11 to 14 are configured by an application specific integrated circuit (ASIC) or the like. However, the present invention is not limited to this case, and all or a part of the functions of the circuits 11 to 14 may be realized by the processing circuitry 18 executing a program.

The transmitting and receiving circuit 11 has a transmitting circuit and a receiving circuit (not shown). Under the control of the processing circuitry 18, the transmitting and receiving circuit 11 controls transmission directivity and reception directivity in transmission and reception of ultrasonic waves. The case where the transmitting and receiving circuit 11 is provided in the ultrasonic diagnostic apparatus 10 will be described, but the transmitting and receiving circuit 11 may be provided in the ultrasonic probe 20, or may be provided in both of the ultrasonic diagnostic apparatus 10 and the ultrasonic probe 20.

The transmitting circuit has a pulse generating circuit, a transmission delay circuit, a pulsar circuit and the like, and supplies a drive signal to ultrasonic transducers. The pulse generating circuit repeatedly generates a rate pulse for forming a transmission ultrasonic wave at a predetermined rate frequency. The transmission delay circuit converges the ultrasonic waves generated from the ultrasonic transducer of the ultrasonic probe 20 into a beam shape, and gives a delay time for each piezoelectric transducer necessary for determining the transmission directivity to each rate pulse generated by the pulse generating circuit. In addition, the pulsar circuit applies a drive pulse to the ultrasonic transducers at a timing based on the rate pulse. The transmission delay circuit arbitrarily adjusts the transmission direction of the ultrasonic beam transmitted from a piezoelectric transducer surface by changing the delay time given to each rate pulse.

The receiving circuit has an amplifier circuit, an A/D (Analog to Digital) converter, an adder, and the like, and receives the echo signal received by the ultrasonic transducers and performs various processes on the echo signal to generate echo data. The amplifier circuit amplifies the echo signal for each channel, and performs gain correction processing. The A/D converter A/D-converts the gain-corrected echo signal, and gives a delay time necessary for determining the reception directivity to the digital data. The adder adds the echo signal processed by the A/D converter to generate echo data. By the addition processing of the adder, the reflection component from the direction corresponding to the reception directivity of the echo signal is emphasized.

Under the control of the processing circuitry 18, the B mode processing circuit 12 receives the echo data from the receiving circuit, performs logarithmic amplification, envelope detection processing and the like, thereby generating data (two-dimensional or three-dimensional data) whose signal intensity is represented by brightness of luminance. This data is generally called B mode data.

Under the control of the processing circuitry 18, the Doppler processing circuit 13 frequency-analyzes the phase information from the echo data from the receiving circuit, and extracts the blood flow or tissue due to the Doppler effect, thereby generating data (two-dimensional or three-dimensional data) obtained by extracting moving state information such as average speed, dispersion, power and the like for multiple points. This data is generally called Doppler data.

Under the control of the processing circuitry 18, the image generating circuit 14 generates an ultrasonic image expressed in a predetermined luminance range as image data based on the echo signal received by the ultrasonic probe 20. For example, the image generating circuit 14 generates a B mode image in which the intensity of the reflected wave is expressed in luminance from the two-dimensional B mode data generated by the B mode processing circuit 12 as the ultrasonic image. Further, the image generating circuit 14 generates, as the ultrasonic image, a color Doppler image representing moving state information from the two-dimensional Doppler data generated by the Doppler processing circuit 13 such as an average velocity image, a dispersed image, a power image, or a combined image thereof.

The image memory 15 includes memory cells in two axial directions per frame, and includes a two-dimensional memory which is a memory having the memory cells for frames. Under the control of the processing circuitry 18, the two-dimensional memory as the image memory 15 stores the ultrasonic image of one frame or the ultrasonic images frames generated by the image generating circuit 14 as two-dimensional image data.

Under the control of the processing circuitry 18, the image generating circuit 14 performs three-dimensional reconstruction on the ultrasonic image arranged in the two-dimensional memory as the image memory 15, if necessary, by interpolation processing, thereby generating an ultrasonic image as volume data in a three-dimensional memory as the image memory 15. As an interpolation processing method, a known technique is used.

The image memory 15 may include a three-dimensional memory which is a memory having memory cells in three axial directions (X-axis, Y-axis, and Z-axis direction). The three-dimensional memory as the image memory 15 stores the ultrasonic image generated by the image generating circuit 14 as volume data under the control of the processing circuitry 18.

The display control circuit 16 includes a graphics processing unit (GPU), a Video RAM (VRAM), and the like. Under the control of the processing circuitry 18, the display control circuit 16 displays the ultrasonic image (for example, a live image), requested for display output from the processing circuitry 18, to the display 40.

The network connection circuit 17 implements various information communication protocols according to the form of the network. In accordance with these various protocols, the network connection circuit 17 connects the ultrasonic diagnostic apparatus 10 and other devices such as the external medical image managing apparatus 50 and the medical image processing apparatus 60. As this connection, electrical connection or the like via an electronic network can be applied. In this embodiment, the electronic network means the whole information communication network using the telecommunication technology, and includes a local area network (LAN) of a wireless/wired hospital core and an internet network, a telephone communication network, an optical fiber communication network, a cable communication network, a satellite communication network, and the like.

Further, the network connection circuit 17 may implement various protocols for non-contact wireless communication. In this case, the ultrasonic diagnostic apparatus 10 can directly exchange data with the ultrasonic probe 20, for example, without going through the network.

The processing circuitry 18 means an ASIC, a programmable logic device, etc. in addition to a dedicated or general purpose central processing unit (CPU), a micro processor unit (MPU), or graphics processing unit (GPU). As the programmable logic device, for example, a simple programmable logic device (SPLD), a complex programmable logic device (CPLD), a field programmable gate array (FPGA).

Further, the processing circuitry 18 may be constituted by a single circuit or a combination of independent circuit elements. In the latter case, the internal memory 19 may be provided individually for each circuit element, or a single internal memory 19 may store programs corresponding to the functions of the circuit elements.

The internal memory 19 is constituted by a semiconductor memory element such as a random access memory (RAM), a flash memory, a hard disk, an optical disk, or the like. The internal memory 19 may be constituted by a portable medium such as a universal serial bus (USB) memory and a digital video disk (DVD). The internal memory 19 stores various processing programs (including an OS (operating system) and the like besides the application program) used in the processing circuitry 18 and data necessary for executing the programs. In addition, the OS may include a graphical user interface (GUI) which allows the operator to frequently use graphics to display information on the display 40 to the operator and can perform basic operations by the input interface 30.

The ultrasonic probe 20 includes microscopic transducers (piezoelectric elements) on the front surface portion, and transmits and receives ultrasonic waves to a region including a scan target, for example, a region including a luminal body. Each transducer is an electroacoustic transducer, and has a function of converting electric pulses into ultrasonic pulses at the time of transmission and converting reflected waves to electric signals (reception signals) at the time of reception. The ultrasonic probe 20 is configured to be small and lightweight, and is connected to the ultrasonic diagnostic apparatus 10 via a cable (or wireless communication).

The ultrasonic probe 20 is classified into types such as a linear type, a convex type, a sector type, etc., depending on a difference in scanning system. The ultrasonic probe 20 is classified into a 1D array probe in which transducers are arrayed in a one-dimensional (1D) manner in the azimuth direction, and a 2D array probe in which transducers are arrayed in two dimensions (2D) manner in the azimuth direction and in the elevation direction, depending on the array arrangement dimension. The 1D array probe includes a probe in which a small number of transducers are arranged in the elevation direction.

In this embodiment, when a 3D scan, that is, a volume scan is executed, the 2D array probe having a scan type such as the linear type, the convex type, the sector type, or the like is used as the ultrasonic probe 20. Alternatively, when the volume scan is executed, the 1D probe having a scan type such as the linear type, the convex type, the sector type and the like and having a mechanism that mechanically oscillates in the elevation direction is used as the ultrasonic probe 20. The latter probe is also called a mechanical 4D probe.

The input interface 30 includes a circuit for inputting a signal from an input device operable by an operator and an input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 30 generates an input signal corresponding to the operation and outputs it to the processing circuitry 18.

The display 40 is constituted by a general display output device such as a liquid crystal display or an organic light emitting diode (OLED) display. The display 40 displays various kinds of information under the control of the processing circuitry 18.

FIG. 1 shows the medical image managing apparatus 50 and the medical image processing apparatus 60 which are external devices of the ultrasonic diagnostic apparatus 10. The medical image managing apparatus 50 is, for example, a digital imaging and communications in medicine (DICOM) server, and is connected to a device such as the ultrasonic diagnostic apparatus 10 so that data can be transmitted and received via the network N. The medical image managing apparatus 50 manages a medical image such as an ultrasonic image generated by the ultrasonic diagnostic apparatus 10 as a DICOM file.

The medical image processing apparatus 60 is connected to devices such as the ultrasonic diagnostic apparatus 10 and the medical image management apparatus 50 so that data is transmitted and received via the network N. An Example of the medical image processing apparatus 60 includes a workstation that performs various image processing on the ultrasonic image generated by the ultrasonic diagnostic apparatus 10 and a portable information processing terminal such as a tablet terminal. It should be noted that the medical image processing apparatus 60 is an offline apparatus and may be an apparatus capable of reading an ultrasonic image generated by the ultrasonic diagnostic apparatus 10 via a portable storage medium.

Subsequently, functions of the ultrasonic diagnostic apparatus 10 will be described.

Figure 2:
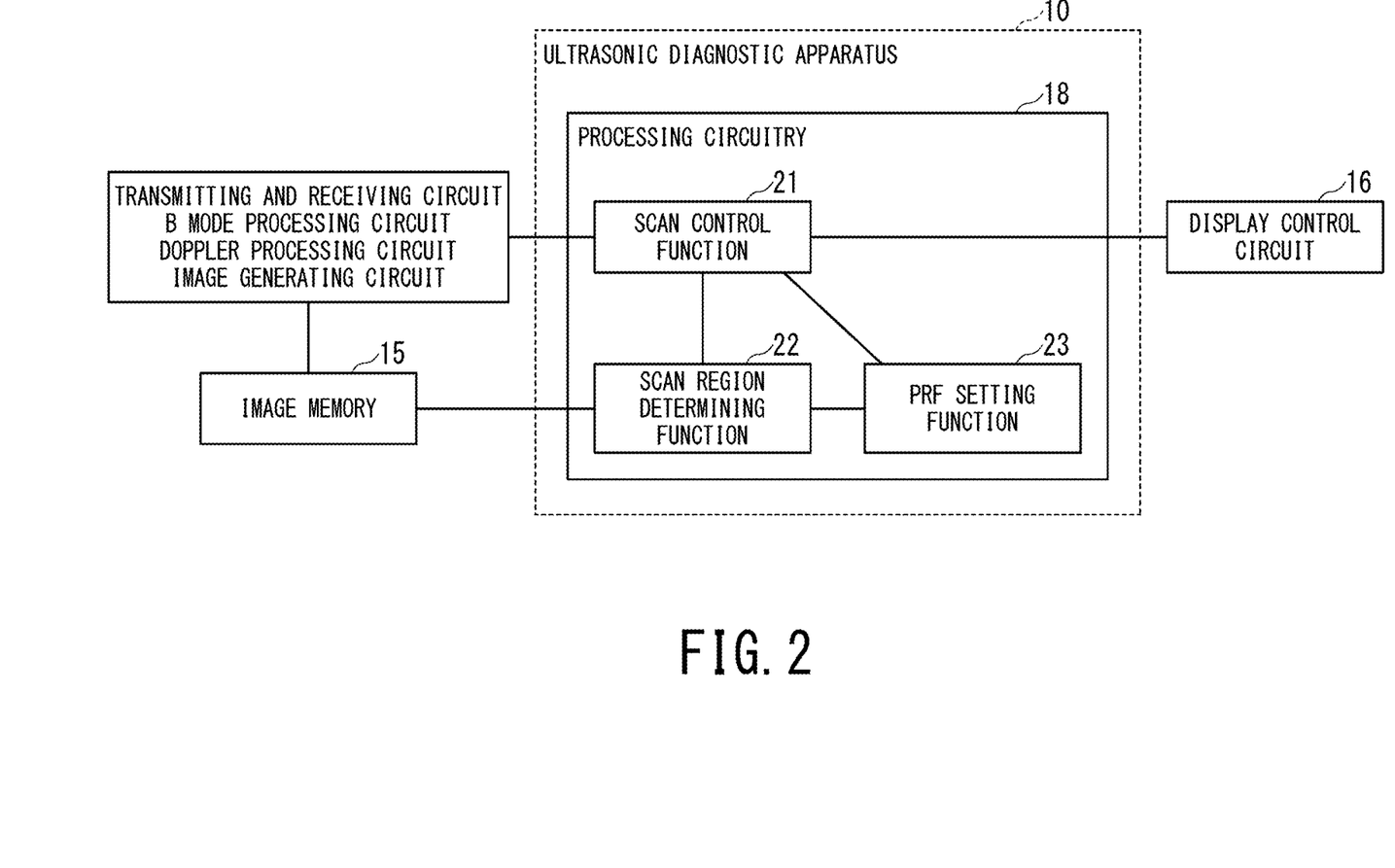
FIG. 2 is a block diagram showing functions of the ultrasonic diagnostic apparatus according to the present embodiment.

FIG. 2 is a block diagram showing functions of the ultrasonic diagnostic apparatus 10.

The processing circuitry 18 reads out and executes a program stored in the internal memory 19 or directly incorporated in the processing circuitry 18, thereby realizing a scan control unit (for example, a scan control function) 21, a determining unit (for example, a scan region determining function) 22, and a setting unit (for example, a PRF setting function) 23. Hereinafter, a case where the functions 21 to 23 function as software will be described as an example. All or a part of the functions 21 to 23 may be provided as a circuit or the like of ASIC etc. in the ultrasonic diagnostic apparatus 10.

The scan control function 21 is a function of controlling to perform scanning according to a preset first PRF or a second PRF set by a later-described PRF setting function 23. The scan control function 21 controls the PRF for at least one of the B mode, the color mode, the Doppler mode, the 3D mode, and the 4D mode.

The scan region determining function 22 is a function of determining a scan region of the ultrasonic waves in accordance with the scan target. For example, the scan region determining function 22 determines the scan region based on the ultrasonic image data generated by performing the scan by the scan control function 21.

The PRF setting function 23 is a function of setting the PRF for each raster of rasters so as to correspond to the scan region determined by the scan region determining function 22.

Details of the functions of the functions 21 to 23 will be described later with reference to FIGS. 3 to 9.

Subsequently, the operation of the ultrasonic diagnostic apparatus 10 will be described.

Figure 3:
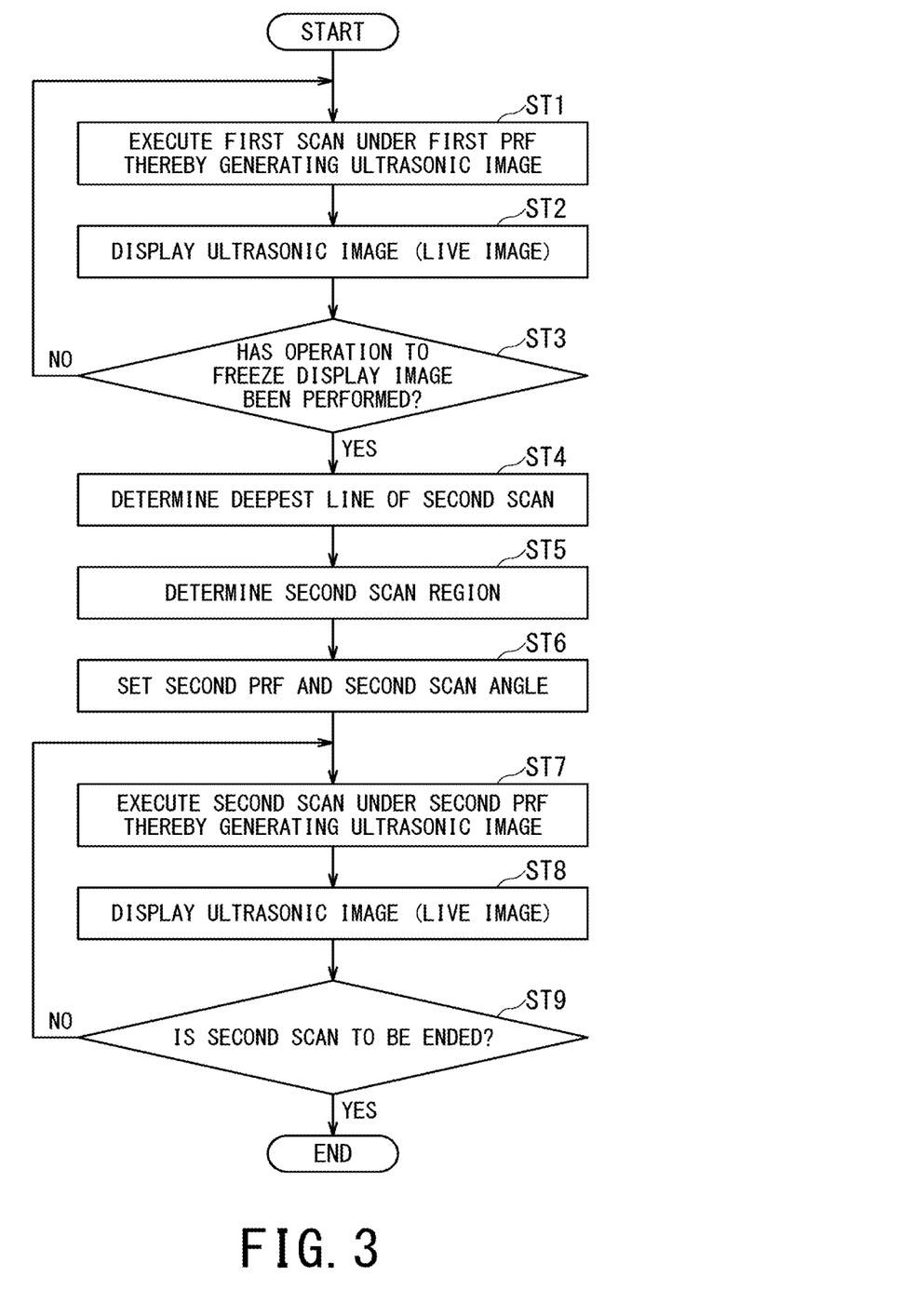
FIG. 3 is a flowchart showing the operation of the ultrasonic diagnostic apparatus according to the present embodiment.
Figure 4A:
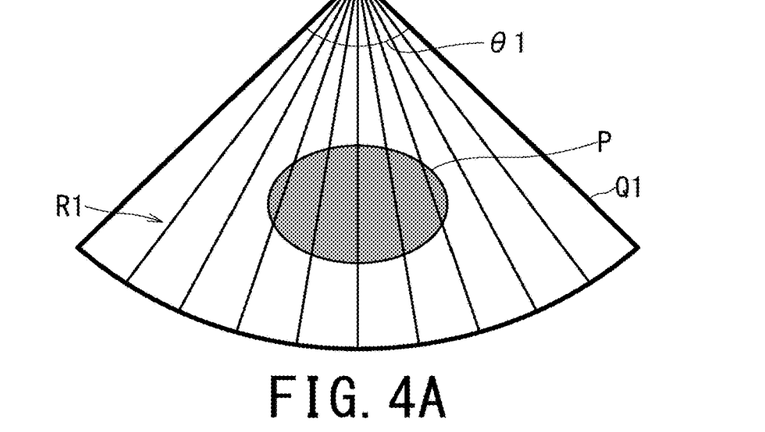
Figure 4B:
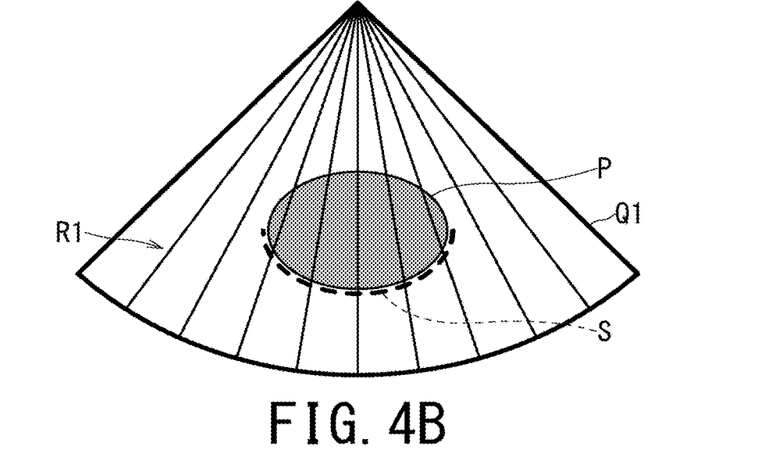
Figure 4C:
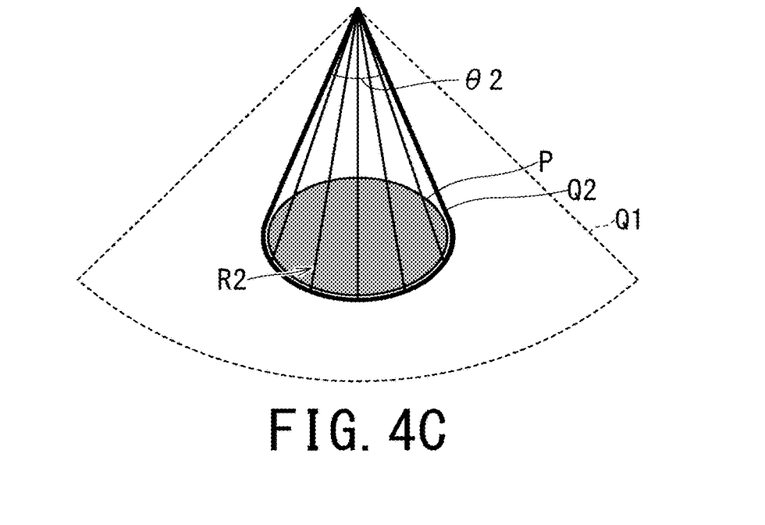

FIG. 3 is a flowchart showing the operation of the ultrasonic diagnostic apparatus 10. In FIG. 3, the reference numerals assigned "ST" with numerals indicate the respective steps of the flowchart. Each of FIGS. 4A to 4C is a diagram for explaining a method for setting a second PRF according to the scan target in the ultrasonic diagnostic apparatus 10. Each of FIGS. 4A to 4C shows the B mode image generated by the 1D array probe having a sector type scanning system.

The scan control function 21 comprehensively controls the transmitting and receiving circuit 11 and the like in accordance with a scan starting instruction from the operator via the input interface 30, and executes a first scan under the first PRF for the first scan region including the scan target of the patient, thereby generating an ultrasonic image including a scan target, for example, a B mode image (step ST1). In step ST1, the scan control function 21 sets the first PRF (that is, the depth of each raster) based on the depth of the first scan region, and sets a first scan angle (that is, the number of rasters) based on the spread of the first scan region.

The scan control function 21 generates and displays, when the first scan is executed in step ST1, the B mode image as a live image (step ST2). The B mode image generated in step ST1 is stored in the image memory 15.

FIG. 4A is a diagram showing a first scan region in the ultrasonic diagnostic apparatus 10.

FIG. 4A shows a scan target P and the first scan region Q1. Further, FIG. 4A shows multiple rasters R1 including the scan target P and having a depth indicating the first PRF and a scan angle θ1. It should be noted that, in FIG. 4A, eleven rasters are shown as the rasters R1 for convenience, but the present invention is not limited to that case.

By transmitting and receiving ultrasonic beams in the rasters R1 within the range of the scan angle θ1, the B mode image related to the first scan region Q1 is acquired.

Returning to the explanation of FIG. 3, the scan control function 21 determines whether temporary stop of ultrasonic transmission and reception is requested, that is, whether or not an instruction to freeze the display image displayed in step ST2 has been performed (Step ST3). For example, when receiving a freeze instruction of the display image from the operator via the input interface 30, the scan control function 21 determines that the instruction to freeze the display image has been performed. If it is determined as "NO" in step ST3, that is, if it is determined that freeze of the displayed image is not requested, for the next frame, the scan control function 21 executes the first scan under the first PRF for the first scan region including the scan target of the patient, thereby generating an ultrasonic image including the scan target (step ST1).

If it is determined as "YES" in step ST3, that is, if it is determined that freeze of the display image is requested, the scan region determining function 22 temporarily stops the ultrasonic transmission and reception, and determines the deepest line of a later-described second scan region based on the display image displayed in step ST2, that is, the latest B mode image (step ST4).

FIG. 4B is a diagram showing the deepest line in the ultrasonic diagnostic apparatus 10.

FIG. 4B shows the scan target P and the deepest line S of the second scan region determined based on the scan target P. First, the deepest line S is automatically set based on luminance values on the respective rasters R1. For example, a position at which the luminance value first exceeds the threshold value from the deepest portion to the shallowest portion on each raster of the rasters R1 is obtained as a contour point of the scan target P. A line connecting the contour points corresponding to the respective rasters R1 is set as a contour line of the scan target P. Then, the contour line is determined as the deepest line S, or the deepest line S is determined so as to have a certain margin with respect to the contour line. In this case, the deepest line S separated by a constant value in the direction of the deepest portion of each raster from the contour is determined.

Alternatively, the maximum luminance value among the luminance values on each raster of the rasters R1 is obtained, and the position of the maximum luminance value is obtained as the contour point of the scan target P. A line connecting the contour points corresponding to the respective rasters R1 is set as the contour line of the scan target P.

Secondly, the deepest line S of the second scan region is manually set by an operator's operation through the input interface 30.

Returning to the explanation of FIG. 3, the scan region determining function 22 determines a second scan region based on the deepest line of the second scan region determined in step ST4 (step ST5). For example, the scan region determining function 22 determines the second scan region so as to include the deepest line of the second scan region determined in step ST4. The PRF setting function 23 sets a second PRF including PRFs set for each raster based on the depth of the second scan region determined in step ST5, and sets a second scan angle based on a spread of the second scan region determined in step ST5 (step ST6).

FIG. 4C is a diagram showing the second scan region in the ultrasonic diagnostic apparatus 10.

FIG. 4C shows the scan target P and the second scan region Q2 including the deepest line S (shown in FIG. 4B) of the second scan region. Further, FIG. 4C shows rasters R2 having a depth indicating the second PRF, and a scan angle θ2 so as to include the scan target P.

By transmitting and receiving ultrasonic beams in the rasters R2 within the range of the scan angle θ2, a B mode image related to the second scan region Q2 is obtained.

The second scan region Q2 shown in FIG. 4C has a shallower depth than the first scan region Q1 shown in FIG. 4A. The second PRF is set by setting the PRF corresponding to the depth of the second scan region Q2 different for each raster. Therefore, in the second scan for transmitting and receiving ultrasonic waves in the second scan region Q2 shown in FIG. 4C, the frame rate is improved by adopting the second PRF including the PRFs set for each raster. The second scan region Q2 shown in FIG. 4C has a narrow scan angle as compared with the first scan region Q1 shown in FIG. 4A. Therefore, in the second scan for transmitting and receiving ultrasonic waves in the second scan region Q2 shown in FIG. 4C, the frame rate is improved.

Returning to the explanation of FIG. 3, the scan control function 21 comprehensively controls the transmitting and receiving circuit 11 and the others in accordance with an instruction of freeze release from the input interface 30, and executes the second scan under the second PRF for the second scan region including the scan target of the patient, thereby generating an ultrasonic image including the scan target (step ST7).

When the scanning is executed in step ST7, the scan control function 21 generates and displays a B mode image as a live image (step ST8). In accordance with a scan ending instruction from the operator via the input interface 30, the scan control function 21 determines whether or not to end the second scan (step ST9). If it is determined as "NO" in step ST9, that is, if it is determined that the second scan is not to be ended, the scan control function 21 executes the second scan under the second PRF for the second scan region including the scan target of the patient for the next frame, thereby generating the ultrasonic image including the scan target (step ST7).

If it is determined as "YES" in step ST9, that is, if it is determined to end the second scan, the second scan is ended.

It should be noted that in steps ST4 to ST6 in FIG. 3, the scan region determining function 22 determines the second scan region after freezing in step ST3, but the present invention is not limited to this case. For example, the scan region determining function 22 may determine the second scan region, the second PRF and the second scan angle each time the B mode image is generated, without freezing. In this case, the scan control function 21 executes the second scan according to second scan regions which changes with the lapse of time (step ST7).

According to the ultrasonic diagnostic apparatus 10, it is possible to change the PRF according to the type of the scan target, and it is possible to change the PRF according to the individual difference even for the same kind of scan target. That is, according to the ultrasonic diagnostic apparatus 10, it is possible to set an appropriate second PRF according to the scan target. Thereby, in the two-dimensional scan, it is possible to shift to the ultrasonic transmission of the next raster without waiting for the echo signal in the deep position which is outside the scan region Q2 and does not contribute to the diagnosis. As a result, it is possible to improve the frame rate of the live image.

Subsequently, a method of setting the second PRF according to the type of the scan target P will be described with reference to FIGS. 5 to 9.

Figure 5A:
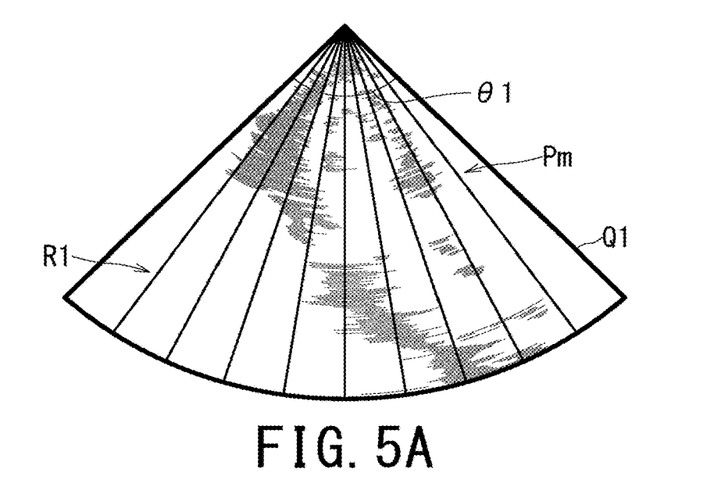
Figure 5B:
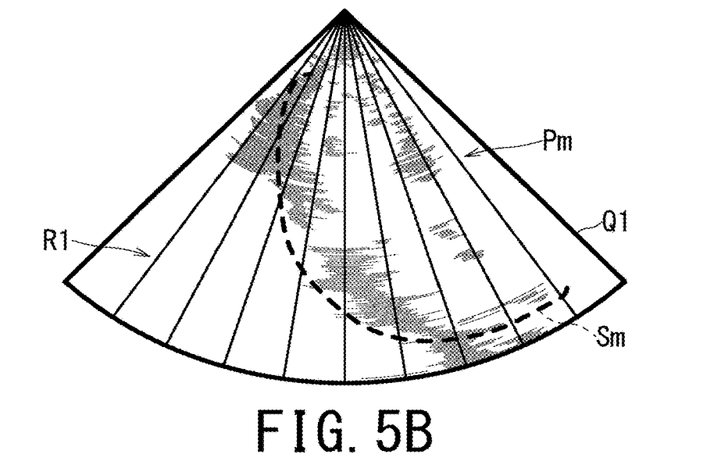
Figure 5C:
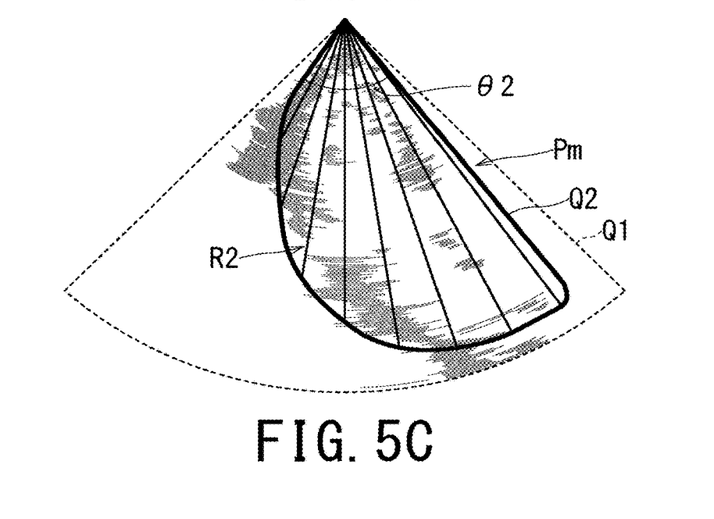

Each of FIGS. 5A to 5C is a diagram for explaining a method for setting the second PRF in the ultrasonic diagnostic apparatus 10 when the scan target is the heart. Each of FIGS. 5A to 5C shows a B mode image generated by the 1D array probe having the sector type scanning system. FIG. 5A is a diagram showing a scan region including the heart in the ultrasonic diagnostic apparatus 10.

FIG. 5A shows the heart Pm as the scan target P and the first scan region Q1. Further, FIG. 5A shows rasters R1 including the heart Pm and having a depth indicating a first PRF and a scan angle θ1. It should be noted that, in FIG. 5A, eleven rasters are shown as the rasters R1 for convenience, but the present invention is not limited to that case.

By transmitting and receiving ultrasonic beams in the rasters R1 within the range of the scan angle θ1, a B mode image related to the first scan region Q1 is obtained.

FIG. 5B is a diagram showing the deepest line of the second scan region based on the heart Pm in the ultrasonic diagnostic apparatus 10.

FIG. 5B shows the heart Pm as the scan target P and the deepest line Sm of the second scan region determined based on the heart Pm. The deepest line Sm is an example of the deepest line S (shown in FIG. 4B). As described above, the deepest line Sm is automatically set based on luminance values on each raster of the rasters R1. Alternatively, as described above, the deepest line Sm is manually set by an operator's operation through the input interface 30.

FIG. 5C is a diagram showing the second scan region based on the heart Pm in the ultrasonic diagnostic apparatus 10.

FIG. 5C shows the heart Pm and a second scan region Q2 including the deepest line Sm (shown in FIG. 5B) of the second scan region. Further, FIG. 5C shows rasters R2 including the heart Pm and having a depth indicating a second PRF, and a scan angle θ2.

By transmitting and receiving ultrasonic beams in the rasters R2 within the range of the scan angle θ2, a B mode image related to the second scan region Q2 is obtained.

The second scan region Q2 shown in FIG. 5C has a shallower depth than the first scan region Q1 shown in FIG. 5A. The second PRF is set by setting for each raster the PRF corresponding to the depth of the second scan region Q2 different for each raster. Therefore, in the second scan for transmitting and receiving ultrasonic waves in the second scan region Q2 shown in FIG. 5C, the frame rate is improved by adopting the second PRF including PRFs set for each raster. Further, the second scan region Q2 shown in FIG. 5C has a narrow scan angle as compared with the first scan region Q1 shown in FIG. 5A. Therefore, in the second scan for transmitting and receiving ultrasonic waves in the second scan region Q2 shown in FIG. 5C, the frame rate is improved.

Figure 6A:
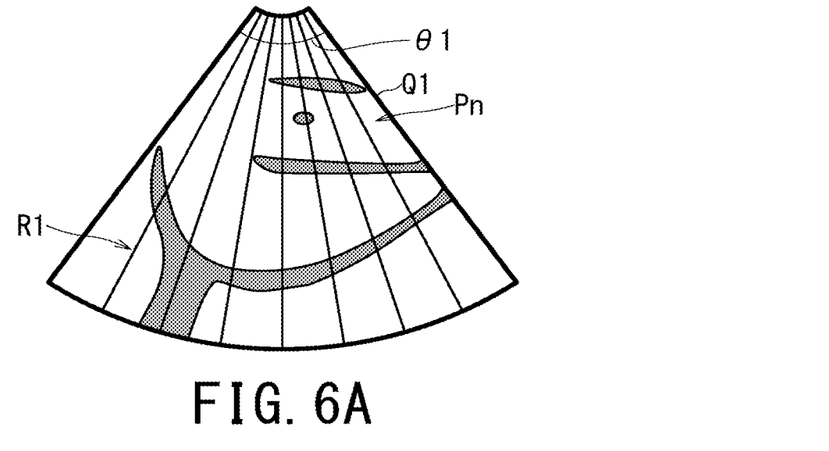
Figure 6B:
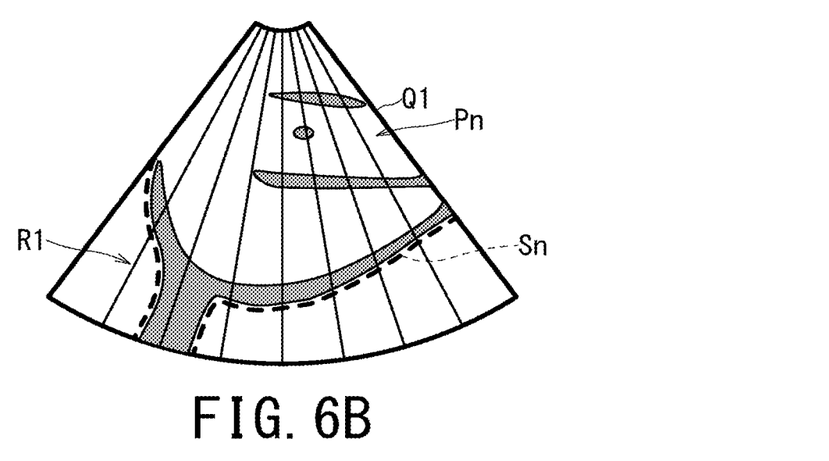
Figure 6C:
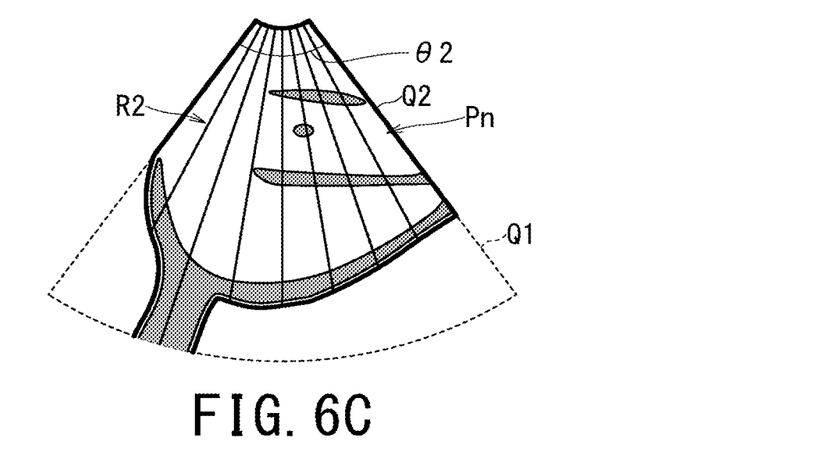

Each of FIGS. 6A to 6C is a diagram for explaining a method for setting the second PRF in the ultrasonic diagnostic apparatus 10 when the scan target is the abdomen. Each of FIGS. 6A to 6C shows a B mode image by the 1D array probe having the convex type scanning system. FIG. 6A is a diagram showing a scan region including the abdomen in the ultrasonic diagnostic apparatus 10.

FIG. 6A shows the abdomen Pn as the scan target P and the first scan region Q1. Further, FIG. 6A shows the rasters R1 including the abdomen Pn, having a depth indicating the first PRF, and a scan angle θ1. In FIG. 6A, nine rasters are shown as the rasters R1 for convenience, but the present invention is not limited to that case.

By transmitting and receiving ultrasonic beams in the rasters R1 within the range of the scan angle θ1, a B mode image related to the first scan region Q1 is obtained.

FIG. 6B is a diagram showing the deepest line of the second scan region based on the abdomen Pn in the ultrasonic diagnostic apparatus 10.

FIG. 6B shows the abdomen Pn as the scan target P and the deepest line Sn of the second scan region determined based on the abdomen Pn. The deepest line Sn is an example of the deepest line S (shown in FIG. 4B). As described above, the deepest line Sn is automatically set based on luminance values on each raster of the rasters R1. Alternatively, as described above, the deepest line Sn is manually set by an operator's operation through the input interface 30.

FIG. 6C is a diagram showing a second scan region based on the abdomen Pn in the ultrasonic diagnostic apparatus 10.

FIG. 6C shows the abdomen Pn and the second scan region Q2 including the deepest line Sn (shown in FIG. 6B) of the second scan region. In addition, FIG. 6C shows rasters R2 including the abdomen Pn, having a depth indicating the second PRF, and a scan angle θ2.

By transmitting and receiving ultrasonic beams in the rasters R2 within the range of the scan angle θ2, a B mode image related to the second scan region Q2 is obtained.

The second scan region Q2 shown in FIG. 6C has a shallower depth than the first scan region Q1 shown in FIG. 6A. The second PRF is set by setting the PRF corresponding to the depth of the second scan region Q2 different for each raster. Therefore, in the second scan for transmitting and receiving ultrasonic waves in the second scan region Q2 shown in FIG. 6C, the frame rate is improved by adopting the second PRF including the PRFs set for each raster. Further, the second scan region Q2 shown in FIG. 6C has the same scan angle (θ1=θ2) as compared with the first scan region Q1 shown in FIG. 6A.

It should be noted that cases where the embodiment is applied to the B mode has been described, but the present invention is not limited to that case. The embodiment can also be applied to the color Doppler mode.

Figure 7A:
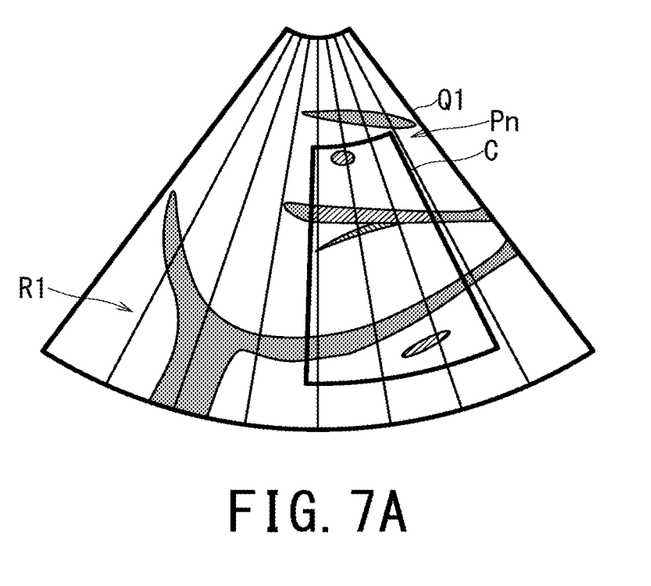
Figure 7B:
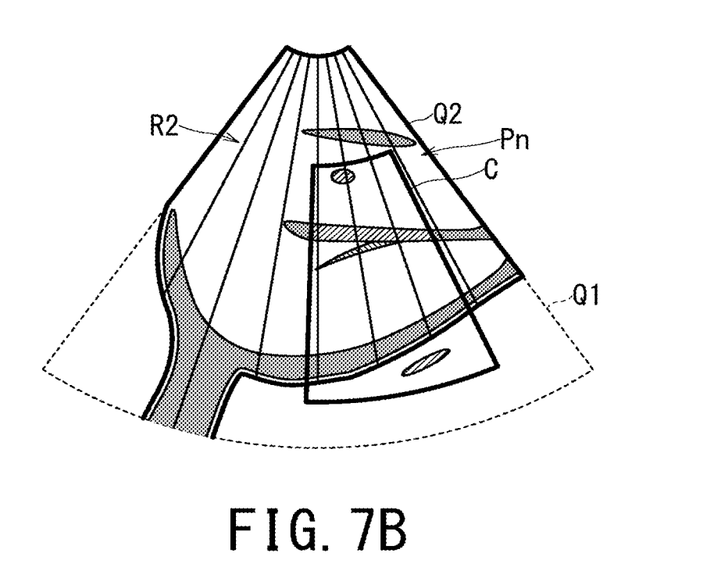

Each of FIGS. 7A and 7B is a diagram for explaining a method for setting the second PRF in the ultrasonic diagnostic apparatus 10 when the scan target is the abdomen. Each of FIGS. 7A and 7B shows a color Doppler image generated by the 1D array probe having the convex scan system. FIG. 7A is a diagram showing a scan region including the abdomen in the ultrasonic diagnostic apparatus 10.

FIG. 7A shows the abdomen Pn as the scan target P and the first scan region Q1. Further, FIG. 7A shows rasters R1 having a depth indicating the first PRF, including the abdomen Pn, and the scan angle θ1. It should be noted that, in FIG. 7A, nine rasters are shown as the rasters R1 for convenience, but the present invention is not limited to this case.

By transmitting and receiving ultrasonic beams in the rasters R1 within the range of the scan angle θ1, a B mode image related to the first scan region Q1 is obtained. Further, an image obtained by the color Doppler mode is superimposed on the color display region C which is a partial region of the B mode image.

FIG. 7B is a diagram showing a second scan region based on the abdomen Pn in the ultrasonic diagnostic apparatus 10.

FIG. 7B shows the abdomen Pn and the second scan region Q2 including the deepest line Sn (shown in FIG. 6B) of the second scan region. Further, FIG. 7B shows rasters R2 including the abdomen Pn, having a depth indicating the second PRF, and a scan angle θ2.

The color display region C includes a portion deeper than the deepest line Sn (diaphragm) of the abdomen. However, even in the color display region C, a portion deeper than the deepest line Sn is not included in the scan region of the color Doppler mode. A past image generated by the first scan related to the first scan region Q1 shown in FIG. 7A may be superimposed on a portion within the color display area C and deeper than the deepest line Sn.

It should be noted that the embodiment is applied to the two-dimensional scan, but it is not limited to that case. The embodiment can also be applied to a three-dimensional scan (or four-dimensional scan) using the 2D probe array or the mechanical 4D probe, that is, a volume scan.

Figure 8A:
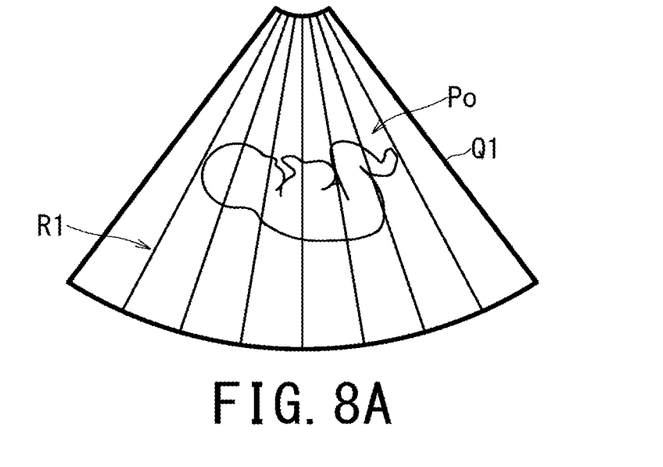
Figure 8B:
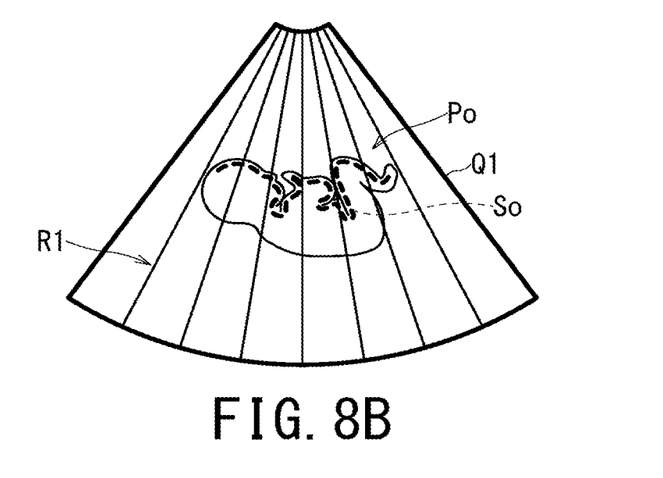
Figure 8C:
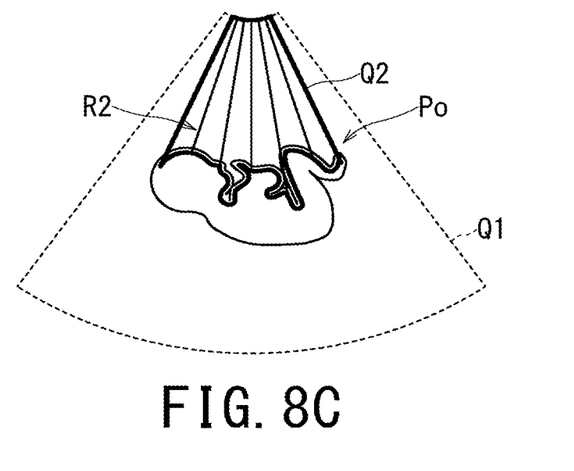

Each of FIGS. 8A to 8C is a diagram for explaining a method for setting the second PRF in the ultrasonic diagnostic apparatus 10 when the scan target is a fetus. FIGS. 4A to 7B show the second scan region in which the portion deeper than the scan target is excluded from the scan region in the case of scanning the entire scan target. On the other hand, each of FIGS. 8A to 8C shows a scan region in which a portion deeper than the scan target is excluded from the scan region in the case of scanning only shallow portion of the scan target.

Each of FIGS. 8A to 8C exemplifies a B-mode image of a certain section generated by the 2D array probe (or a mechanical 4D probe) having the convex type scanning system. FIG. 8A is a diagram showing a scan region including a fetus in the ultrasonic diagnostic apparatus 10.

FIG. 8A shows a fetus Po as a scan target P in a certain cross section and a first scan region Q1. Further, FIG. 8A shows rasters R1 including the fetus Po and having a depth indicating the first PRF and a scan angle θ1. It should be noted that, in FIG. 8A, nine rasters are shown as the rasters R1 for convenience, but the present invention is not limited to that case.

By transmitting and receiving ultrasonic beams in the rasters R1 within the range of the scan angle θ1, a B mode image related to the first scan region Q1 is obtained.

FIG. 8B is a diagram showing the deepest line of the second scan region based on the fetus Po in the ultrasonic diagnostic apparatus 10.

FIG. 8B shows the fetus Po as the scan target P and the deepest line So of the second scan region determined based on the fetus Po. The deepest line So is an example of the deepest line S (shown in FIG. 4B). First, the deepest line So is automatically set based on luminance values on each raster of the rasters R1. For example, a position at which the luminance value first exceeds the threshold value from the shallowest portion to the deepest portion on each raster of the rasters R1 is obtained as the contour point of the fetus Po. A line connecting contour points corresponding to the respective rasters R1 is set as the contour line of the fetus Po. Then, the deepest line So is determined so as to have a certain margin with respect to the contour line. In that case, the deepest line So distant from the contour by a certain value in the direction of the deepest part of each raster is determined.

Alternatively, the maximum luminance value among the luminance values on each raster of the rasters R1 is obtained, and the position of the maximum luminance value is obtained as the contour point of the fetus Po. A line connecting the contour points corresponding to the respective rasters R1 is set as the contour line of the fetus Po. Alternatively, the contour of the fetus Po may be set by pattern matching based on past images corresponding to the fetus Po.

Secondary, the deepest line So of the second scan region is manually set by an operator's operation through the input interface 30.

FIG. 8C is a diagram showing the second scan region based on the fetus Po in the ultrasonic diagnostic apparatus 10.

FIG. 8C shows a fetus Po and a second scan region Q2 including the deepest line So (FIG. 8B) of the second scan region. FIG. 8C shows rasters R2 including a fetus Po and having a depth indicating a second PRF, and a scan angle θ2.

By transmitting and receiving ultrasonic beams in the rasters R2 within the range of the scan angle θ2, a B mode image related to the second scan region Q2 is obtained.

In the volume scan, the setting of the second scan region Q2 in the cross section shown in FIGS. 8A to 8C is performed for each of the cross sections in the elevation direction.

The second scan region Q2 shown in FIG. 8C has a shallower depth than the first scan region Q1 shown in FIG. 8A. The second PRF is set by setting the PRF corresponding to the depth of the second scan region Q2 different for each raster. Therefore, in the second scan for transmitting and receiving ultrasonic waves in the second scan region Q2 shown in FIG. 8C, the volume rate is improved by adopting the second PRF including the PRFs set for each raster. Further, the second scan region Q2 shown in FIG. 8C has a narrow scan angle as compared with the first scan region Q1 shown in FIG. 8A. Therefore, in the second scan for transmitting and receiving ultrasonic waves in the second scan region Q2 shown in FIG. 8C, the volume rate is improved.

Figure 9:
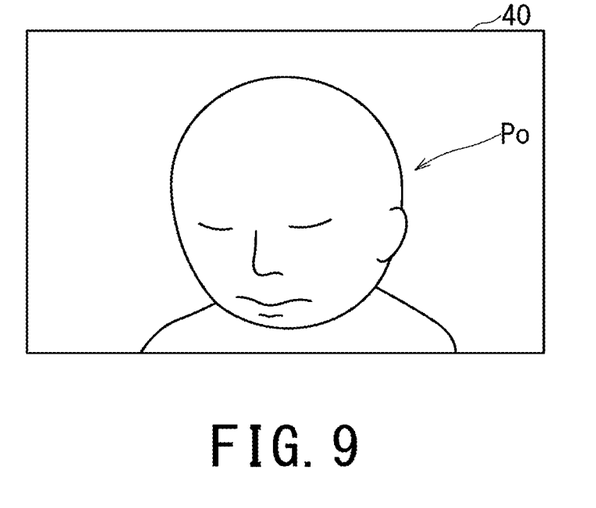
FIG. 9 is a diagram showing an example of a three-dimensional image generated in the ultrasonic diagnostic apparatus according to the present embodiment when the fetus is scanned with the second PRF.

FIG. 9 is a diagram showing an example of a three-dimensional image generated in the ultrasonic diagnostic apparatus 10 when the fetus Po is scanned with the second PRF.

FIG. 9 shows a three-dimensional image obtained by surface rendering processing on B-mode images generated when the volume scan is performed by the second scan region Q2 (shown in FIG. 8C). In this way, the expression of the face of the fetus can be presented to the operator.

As described with reference to FIGS. 5 to 9, according to the ultrasonic diagnostic apparatus 10, it is possible to change the PRF according to the type of the scan target, and even for the same type of scan target, depending on the individual difference PRF can be changed. That is, according to the ultrasonic diagnostic apparatus 10, it is possible to set an appropriate second PRF according to the scan target. Thereby, in the three-dimensional scan, it is possible to shift to the ultrasonic transmission of the next raster and the next cross section without waiting for the echo signal in the deep position which is outside the scan region Q2 and does not contribute to the diagnosis. As a result, it is possible to improve the volume rate of the live image.

2. Method for Determining Deepest Line of Second Scan Region

In step ST4 of FIG. 3, the scan region determining function 22 has described the case of determining the deepest line of the second scan region, based on the position (shown in FIGS. 4A to 7B) where the luminance value first exceeds the threshold value from the deepest portion to the shallowest portion on each raster, or based on the position (shown in FIGS. 8A to 8C) where the luminance value first exceeds the threshold value from the shallowest portion to the deepest portion on each raster. However, the method of determining the deepest line is not limited to those cases.

For example, the scan region determining function 22 may use the pattern matching between an atlas image (for example, a typical B mode image) and the B mode image generated and displayed at step ST2, thereby setting the deepest line of the second scan region. Alternatively, the scan region determining function 22 may manually determine the deepest line of the second scan region by an operator's operation via the input interface 30. In addition, the scan region determining function 22 may manually correct the deepest line determined by the luminance value processing and the pattern matching described above by an operation of an operator via the input interface 30, thereby determine the deepest line of the second scan region.

3. Method for Scanning in Second Scan Region

As described above, the scan control function 21 employs the second PRF for rasters in the second scan region and performs ultrasonic transmission and reception. The sequence of executing ultrasonic transmissions corresponding to the respective rasters in the second scan region will be described.

Figure 10A:
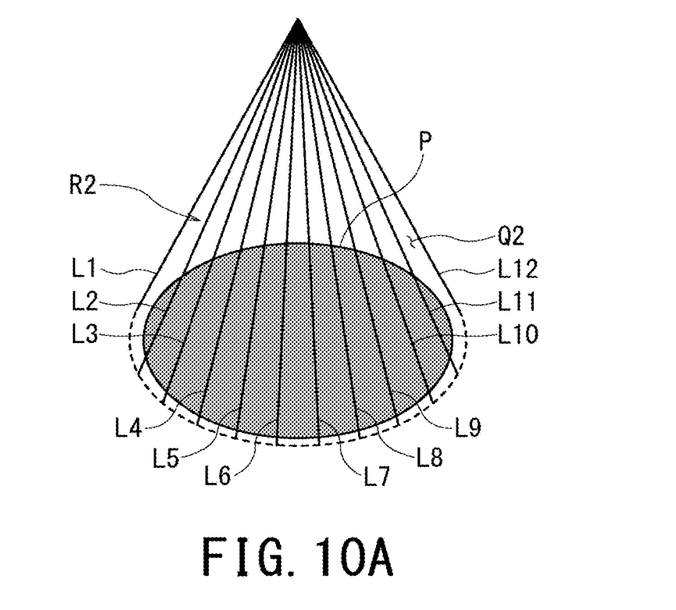
Figure 10B:
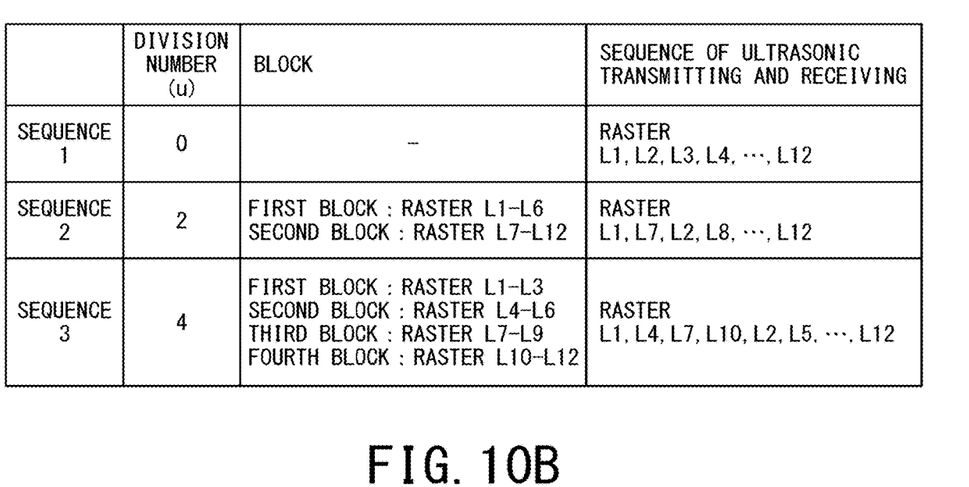

Each of FIGS. 10A to 10C is a diagram showing a sequence of ultrasonic transmission and reception performed in the rasters in the second scan region.

FIG. 10A shows rasters R2 in the second scan region Q2, for example, twelve rasters L1 to L12. The number of rasters is twelve for convenience of explanation, but it is not limited to that number. Further, FIG. 10B is a table showing the execution sequence of twelve ultrasonic transmission and reception executed by twelve rasters L1 to L12.

The sequence 1 in FIG. 10B is a sequence of execution when twelve rasters L1 to L12 shown in FIG. 10A are used to transmit and receive twelve ultrasonic waves from one end raster L1 to the other end raster L12.

When using the second PRF in the second scan region Q2, particularly in a case of a tissue harmonic imaging (THI) or color mode, or in a case of scanning only the shallow portion to be scanned shown in FIGS. 8A to 8C, residual multiplexing may occur in the sequence 1 of FIG. 10B. That is, in the sequence 1, there is a problem that a reflected wave from a deep part outside the second scan region Q2 is received at the time of reception of a reflected wave at the adjacent raster by transmission of ultrasonic waves at a certain raster.

Therefore, as shown in sequences 2 and 3 in FIG. 10B, when the twelve rasters L1 to L12 in the second scan region Q2 are used, it is preferable that the scan control function 21 sequentially transmits and receives twelve ultrasonic waves to and from the rasters that are separated by a predetermined interval.

Specifically, the scan control function 21 divides the twelve rasters L1 to L12 in the second scan region Q2 into u (u: an integer equal to or larger than two) blocks, and executes ultrasonic transmission and reception sequentially to u blocks and sequentially to the rasters in each block. It should be noted that the sequence 2 of FIG. 10B shows the case of u=2, and the sequence 3 of FIG. 10B shows the case of u=4.

In the case of the sequence 2, the scan control function 21 divides the twelve rasters L1 to L12 into a first block of six rasters L1 to L6 and a second block of six rasters L7 to L12. The scan control function 21 executes the ultrasonic transmission and reception alternately to the first block and the second block, and sequentially to the six rasters in each block. In this case, the scan control function 21 executes twelve ultrasonic transmission and reception per unit scan while adopting the second PRF in the order of the rasters L1, L7, L2, L8, . . . , L12.

In the case of the sequence 3, the scan control function 21 divides the twelve rasters L1 to L12 into a first block of three rasters L1 to L3, a second block of three rasters L4 to L6, a third block of three rasters L7 to L9 and a fourth block of three rasters L10 to L12. The scan control function 21 executes ultrasonic transmission and reception sequentially to the first to fourth blocks, and sequentially to the three rasters in each block. In this case, the scan control function 21 executes twelve ultrasonic transmission and reception per unit scan while adopting the second PRF in the order of the rasters L1, L4, L7, L10, L2, L5, . . . , L12.

According to at least one of the embodiments described above, it is possible to set an appropriate PRF according to the scan target.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
processing circuitry configured to
determine a scan region of an ultrasonic wave based on ultrasonic image data generated by performing an ultrasonic scan according to a scan target,
set a depth for each raster of a plurality of rasters to include the scan region, thereby changing the depth on a raster-by-raster basis,
set a contour line of the scan target for the plurality of rasters in the scan region based on the ultrasonic image data by obtaining a position at which a luminance value first exceeds a threshold value from a deepest portion to a shallowest portion on each raster of the plurality of rasters as a contour point of the scan target, and setting a line connecting the contour points corresponding to the respective rasters of plurality of rasters as the contour line;
determine the scan region based on the contour line;
set a pulse repetition frequency for each raster of the plurality of rasters based on the depth for each raster, thereby changing the pulse repetition frequency on the raster-by-raster basis, and
control an ultrasonic scan performance according to the changing pulse repetition frequency on the raster-by-raster basis.

2. The ultrasonic diagnostic apparatus according to claim 1, wherein the processing circuitry is configured to determine the scan region by an operation through an input device.

3. The ultrasonic diagnostic apparatus according to claim 1, wherein the processing circuitry is configured to determine the scan region to include the contour line.

4. The ultrasonic diagnostic apparatus according to claim 1, wherein the processing circuitry is configured to determine the scan region to include a position deeper than the contour line by a fixed value.

5. The ultrasonic diagnostic apparatus according to claim 1, wherein the processing circuitry is configured to
divide the plurality of rasters in the scan region into blocks, and
execute transmission and reception of ultrasonic waves sequentially to the blocks and sequentially to respective rasters of plurality of rasters in each block of the blocks.

6. The ultrasonic diagnostic apparatus according to claim 5, wherein the processing circuitry is configured to
divide the plurality of rasters in the scan region into two blocks, and
execute transmission and reception of ultrasonic waves alternately to the two blocks and sequentially to respective rasters of the plurality of rasters in each block of the two blocks.

7. The ultrasonic diagnostic apparatus according to claim 1, wherein the processing circuitry is configured to
set the pulse repetition frequency for each raster of the plurality of rasters so as to correspond to the scan region based on a depth of the scan region, and
set an ultrasonic scan angle based on a spread of the scan region.

8. The ultrasonic diagnostic apparatus according to claim 1, wherein the processing circuitry is configured to set the pulse repetition frequency for at least one of B mode, color mode, Doppler mode, 3D mode, and 4D mode.

9. An ultrasonic diagnostic apparatus comprising:
processing circuitry configured to
determine a scan region of an ultrasonic wave based on ultrasonic image data generated by performing an ultrasonic scan according to a scan target,
set a depth for each raster of a plurality of rasters to include the scan region, thereby changing the depth on a raster-by-raster basis,
set a contour line of the scan target for the plurality of rasters in the scan region based on the ultrasonic image data by obtaining a position at which a luminance value first exceeds a threshold value from a shallowest portion to a deepest portion on each raster of the plurality of rasters as a contour point of the scan target, and setting a line connecting the contour points corresponding to the respective rasters of the plurality of rasters as the contour line,
determine the scan region based on the contour line;
set a pulse repetition frequency for each raster of the plurality of rasters based on the depth for each raster, thereby changing the pulse repetition frequency on the raster-by-raster basis, and
control an ultrasonic scan performance according to the changing pulse repetition frequency on the raster-by-raster basis.

10. The ultrasonic diagnostic apparatus according to claim 9, wherein the processing circuitry is configured to determine the scan region to include a position deeper than the contour line by a fixed value.

11. A method for controlling a pulse repetition frequency comprising:
determining a scan region of an ultrasonic wave based on ultrasonic image data generated by performing an ultrasonic scan according to a scan target;
setting a depth for each raster of a plurality of rasters to include the scan region, thereby changing the depth on a raster-by-raster basis;
setting a contour line of the scan target for the plurality of rasters in the scan region based on the ultrasonic image data by obtaining a position at which a luminance value first exceeds a threshold value from a deepest portion to a shallowest portion on each raster of the plurality of rasters as a contour point of the scan target, and setting a line connecting the contour points corresponding to the respective rasters of plurality of rasters as the contour line;
determining the scan region based on the contour line;
setting the pulse repetition frequency for each raster of the plurality of rasters based on the depth for each raster, thereby changing the pulse repetition frequency on the raster-by-raster basis; and
controlling an ultrasonic scan performance according to the changing pulse repetition frequency on the raster-by-raster basis.

12. The method according to claim 11, wherein determining the scan region of the ultrasonic wave according to the scan target further comprises determining the scan region by an operation through an input device.

13. The method according to claim 11, wherein determining the scan region comprises determining the scan region to include a position deeper than the contour line by a fixed value.

14. A method for controlling a pulse repetition frequency comprising:
determining a scan region of an ultrasonic wave based on ultrasonic image data generated by performing an ultrasonic scan according to a scan target;
setting a depth for each raster of a plurality of rasters to include the scan region, thereby changing the depth on a raster-by-raster basis;
setting a contour line of the scan target for the plurality of rasters in the scan region based on the ultrasonic image data by obtaining a position at which a luminance value first exceeds a threshold value from a shallowest portion to a deepest portion on each raster of the plurality of rasters as a contour point of the scan target, and setting a line connecting the contour points corresponding to the respective rasters of the plurality of rasters as the contour line;
determining the scan region based on the contour line;
setting the pulse repetition frequency for each raster of the plurality of rasters based on the depth for each raster, thereby changing the pulse repetition frequency on the raster-by-raster basis; and
controlling an ultrasonic scan performance according to the changing pulse repetition frequency on the raster-by-raster basis.

* * * * *